(12) United States Patent
Licata et al.

(10) Patent No.: US 6,510,333 B1
(45) Date of Patent: Jan. 21, 2003

(54) SENSOR FOR BIOPOTENTIAL MEASUREMENTS

(76) Inventors: Mark J. Licata, 11504 River Edge Rd., Doswell, VA (US) 23047; James Mitchell, 12604 Swanhurst Cir., Midlothian, VA (US) 23113

( * ) Notice: Subject to any disclaimer, the term of this patent is extended or adjusted under 35 U.S.C. 154(b) by 79 days.

(21) Appl. No.: 09/773,921

(22) Filed: Feb. 2, 2001

(Under 37 CFR 1.47)

Related U.S. Application Data

(60) Provisional application No. 60/204,603, filed on May 16, 2000.

(51) Int. Cl.⁷ .............................................. A61B 5/0478
(52) U.S. Cl. .................. 600/383; 600/393; 600/396; 600/397; 607/139; 607/148; 607/153
(58) Field of Search ................................. 600/383, 396, 600/397, 393; 607/139, 148, 153

(56) References Cited

U.S. PATENT DOCUMENTS

| | | |
|---|---|---|
| 725,731 A | 4/1903 | Linn |
| 1,099,062 A | 6/1914 | Laposkey |
| 1,667,817 A | 5/1928 | Noishiki |
| 3,508,541 A | 4/1970 | Westbrook et al. |
| 3,580,239 A | 5/1971 | Wantanabe et al. |
| 3,669,110 A * | 6/1972 | Low .......................... 600/397 |
| 3,788,317 A | 1/1974 | McCormick |
| 3,868,947 A | 3/1975 | Holsinger |
| 3,896,790 A | 7/1975 | Dikmen |
| 3,967,628 A * | 7/1976 | Vredenbregt ................ 607/153 |
| 3,989,036 A | 11/1976 | Sasamori |
| 3,998,213 A | 12/1976 | Price |
| 4,033,334 A * | 7/1977 | Fletcher ...................... 600/397 |
| 4,079,731 A | 3/1978 | Danby |
| 4,109,648 A | 8/1978 | Larke et al. |
| 4,126,126 A | 11/1978 | Bare et al. |
| 4,195,626 A | 4/1980 | Schweizer |
| 4,458,687 A * | 7/1984 | Dickson ..................... 600/397 |
| 4,683,892 A | 8/1987 | Johansson et al. |
| 4,685,466 A | 8/1987 | Rau |
| 4,706,679 A | 11/1987 | Schmidt et al. |
| 4,735,207 A | 4/1988 | Nambu et al. |
| 4,919,648 A | 4/1990 | Sibalis |
| 4,967,038 A | 10/1990 | Gevins et al. |
| 5,038,782 A | 8/1991 | Gevins et al. |
| 5,211,184 A | 5/1993 | Yee et al. |
| 5,299,572 A | 4/1994 | Chen et al. |
| 5,305,746 A | 4/1994 | Fenrock |
| 5,309,909 A | 5/1994 | Gadsby et al. |
| 5,348,006 A | 9/1994 | Tucker |
| 5,433,559 A | 7/1995 | Chen et al. |
| 5,724,984 A | 3/1998 | Arnold et al. |
| 6,067,464 A | 5/2000 | Musha |

FOREIGN PATENT DOCUMENTS

| | | | |
|---|---|---|---|
| DE | 2921858 | * 11/1980 | ................ 600/397 |
| GB | 2274396 | * 7/1994 | ................ 600/397 |

* cited by examiner

*Primary Examiner*—Lee Cohen
(74) *Attorney, Agent, or Firm*—John H. Thomas, P.C.

(57) ABSTRACT

A sensor for biopotential measurements is designed to detect low voltage electrical signals on a subject's skin surface. A plurality of soft elastomeric bristles are arranged about the surface of the skin. Various bristles contain a wick, made of polyolefin, polyester or nylon, extending along its center axis with one end protruding from the bristle and another end in contact with a fluid reservoir. The wick is saturated with an electrically conductive liquid, such as a salt solution. The solution may contain a surfactant. The rheological properties of the electrically conductive liquid are optimized for predictable flow through the wick onto the skin surface. An electrode is positioned in the vicinity of the wick and the reservoir. Alternatively, a sensor comprises a plurality of hollow, soft elastomeric bristles filled with a hydrogel. An electrically conductive cap provides the electrical contact between the hydrogel and the electrical circuit.

21 Claims, 7 Drawing Sheets

SENSOR FOR BIOPOTENTIAL MEASUREMENTS

CROSS-REFERENCE TO RELATED APPLICATION

The present application claims the benefit of priority to provisional patent application Ser. No. 60/204,603 to Mark Licata and James Mitchell, filed on May 16, 2000, entitled "Electrode For Biopotential Measurements", which is hereby incorporated by reference.

TECHNICAL FIELD

This invention relates generally to the field of sensors for measuring electrical potentials obtained from the surface of the skin, for example, electroencephalogram (EEG), electrocardiogram (ECG), or electromyogram (EMG).

BACKGROUND OF THE INVENTION

In the past, electroencephalogram (EEG), electrocardiogram (ECG), and electromyogram (EMG) electrodes have needed the assistance of technicians for proper use, and thus have been relegated for use in clinical environments. With the advent of new modem electronic devices, there has developed a need for an electrode sensor that patients may use at home. These new devices allow patients to use new portable medical devices that require electrodes. The electrode needs to be non interfering with the patients hair and needs to be designed so that its use does not require chemicals or gels that can leave a mess. The prior art does not satisfy these requirements.

U.S. Pat. No. 3,508,541, entitled "Electrode Construction" to R. M. Westbrook et al. discloses an electrode device comprising an electrode element formed of an intimately bonded homogeneous mixture of finely divided Ag and AgCl. An elongated resilient skin engaging member, such as a disposable hollow sponge, holds an electrolyte, such as a sodium chloride gel. Additionally, Westbrook et al. discloses an electrode device which is simply applied to the scalp, eliminates motion artifacts, and regardless of such factors as hair tonics, sunburn, hair length/thickness, or perspiration obtains a good, low impedance, contact. The electrode of Westbrook et al. makes no suggestion that a plurality of the elongated resilient skin engaging members would be beneficial in achieving improved contact, and the electrode device configuration is complicated and would be expensive to mass produce.

U.S. Pat. No. 4,195,626 to Schweizer entitled "Device for the Production and Application of Body Stimuli Devices", discloses a biofeedback chamber for applying stimuli and for measuring and analyzing a subject's reaction to control the stimuli. One of the stimulus applicators is a flexible laminar electrode comprising a plurality of reinforced filament bundles, a hollow reservoir and a porous reservoir for holding an electrolyte, and a metal conductor embedded in the porous reservoir. The filament bundles provide capillary action to deliver electrolyte from the porous reservoir to a patient's skin. Besides the fact that Schweizer's disclosure is directed to an electrode for a stimulus applicator as opposed to an electrode for measuring biopotentials, Schweizer teaches away from the present invention in that a flexible laminar electrode is formed of a flexible support, two plastic sheets, yet the filament bundles are stiffened with a reinforcement jacket.

U.S. Pat. No. 4,967,038 to Gevins et al. entitled "Dry Electrode Brain wave Recording System", discloses a semi-rigid helmet containing a plurality of rubber multi-contact electrodes. The electrodes comprise a gold-plated metal pin with one end formed in a rubber base. A plurality of pyramid-shaped rubber fingers, extending from the base, are terminated with conductive round metal tips. Metal flexible wire, attached at a solder point to the pin within the base, extends through the center of each finger to their tips. The flexibility of the multiple fingers allows the electrode to adapt to the local contours of a head. Having redundant, multiple contact points with the scalp improves the connection since it is not dependent on the impedance at a single small point. The rubber multi-contact electrodes of Gevins et al. do not incorporate a mechanism for applying an electrolyte to the scalp in order to improve electrical contact, improve comfort by moistening the skin, and reducing the electrical resistance of the skin. Additionally, Gevens et al. requires electrical conductivity in each of the fingers of their electrode.

U.S. Pat. No. 5,211,184 to Yee et al., entitled "Method and Apparatus For Acupuncture Treatment", discloses an electrode assembly for applying an electrical signal to the skin surface. The electrode assembly comprises a hollow body filled with an electrically conductive fluid, a wick-like material for delivering the fluid to a point where one end of the material is in contact with the skin surface, and a metallic cap attached to a second end of the material. Besides the fact that the Yee et al. disclosure is directed to an electrode for applying an electrical signal as opposed to an electrode for measuring biopotentials, there is no suggestion that a plurality of wicks extending from the hollow body would be beneficial in achieving improved contact with the skin surface.

U.S. Pat. No. 6,067,464 to Musha, entitled "Electrode", discloses an electrode for measuring bio-electric waves. The electrode comprises a support member, a piece of absorbent fiber, and a non-corrosive lead. The support member, made of an insulating material such as ceramic, plastic or heat treated synthetic fibers or felt, is disk-shaped with a hollow, concentric cylindrical projection. The absorbent fiber, made of felt, cotton or synthetic fibers, is mounted in the projection on the support with one end extending beyond the edge of the projection. Alternatively, the absorbent fiber may comprise a bundle of carbon powder impregnated hard felt rods with rounded tips. Electrically conductive fluid, such as saline solution, is introduced into the support through an insertion hole formed opposite the projection, and is absorbed by the absorbent fiber. The electrically conductive fluid may also comprise various skin conditioners, counter-irritant materials, anti-inflammatory agents, and astringents. A lead, made of a bundle of carbon fibers, makes contact with the absorbent fiber through the wall of the projection. Musha teaches away from the present invention by incorporating an insertion hole for introducing electrically conductive fluid into the electrode before and during use as opposed to including a reservoir for holding sufficient electrically conductive fluid for the life of the electrode. Additionally, there is no suggestion that a support comprising a plurality of projections, each with an absorbent fiber, would be beneficial in achieving improved contact with the skin surface.

These conventional sensor configurations described above each fail to disclose at least a single significant attribute of the present invention. What is needed is an electrode which may be used on open skin, or skin covered with hair, does not require the use of external gels or waxes to obtain adequate electrical conduction to the skin surface, may be comfortably worn for long periods of time, and may be properly applied to an individual's scalp without the assistance of a technician.

BRIEF SUMMARY OF THE INVENTION

One advantage of the invention is that it provides a sensor which can be used on open skin, or skin covered with hair and does not require the use of external gels or waxes to obtain adequate electrical conduction to the skin surface.

Another advantage of the present invention is that it provides a sensor which can be comfortably worn for long periods of time.

Yet, another advantage of the present invention is that it provides a sensor which can be applied by the individual wearing the sensor. Hence, no technician is required.

To achieve the foregoing and other advantages, in accordance with all of the invention as embodied and broadly described herein, a sensor for biopotential measurements comprising at least one elastomeric bristle having a base and a tip with a channel running therebetween and a porous wick extending through the channel, the tip contacting a skin surface; a reservoir containing an electrically conductive material is formed at the base of said elastomeric bristle; and an electrode for detecting electrical potential. The porous wick transports the electrically conductive material from the reservoir to the elastomeric bristle tip in order to conduct an electrical signal obtained from the skin surface, moisten the skin surface, and reduce the electrical resistance of the skin surface.

In yet a further aspect of the invention, a sensor for biopotential measurements wherein the reservoir is formed of at least one of: a porous material; and a hollow vessel capable of holding an electrically conductive liquid. The Theological properties of the electrically conductive liquid may be optimized for predictable flow through the porous wick onto the skin surface.

In yet a further aspect of the invention, a sensor for biopotential measurements comprising: a plurality of physically linked and electrically isolated elastomeric bristles, each having a base and a tip with a channel running therebetween, the tip contacting a skin surface; and an electrode for detecting electrical potential. The channel may be filled with a hydrogel material which is formulated to have high electrical conductivity in order to conduct an electrical signal obtained from the skin surface, moisten the skin surface, and reduce the electrical resistance of the skin surface.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate an embodiment of the present invention and, together with the description, serve to explain the principles of the invention.

DETAILED DESCRIPTION OF THE INVENTION

Figure 1:
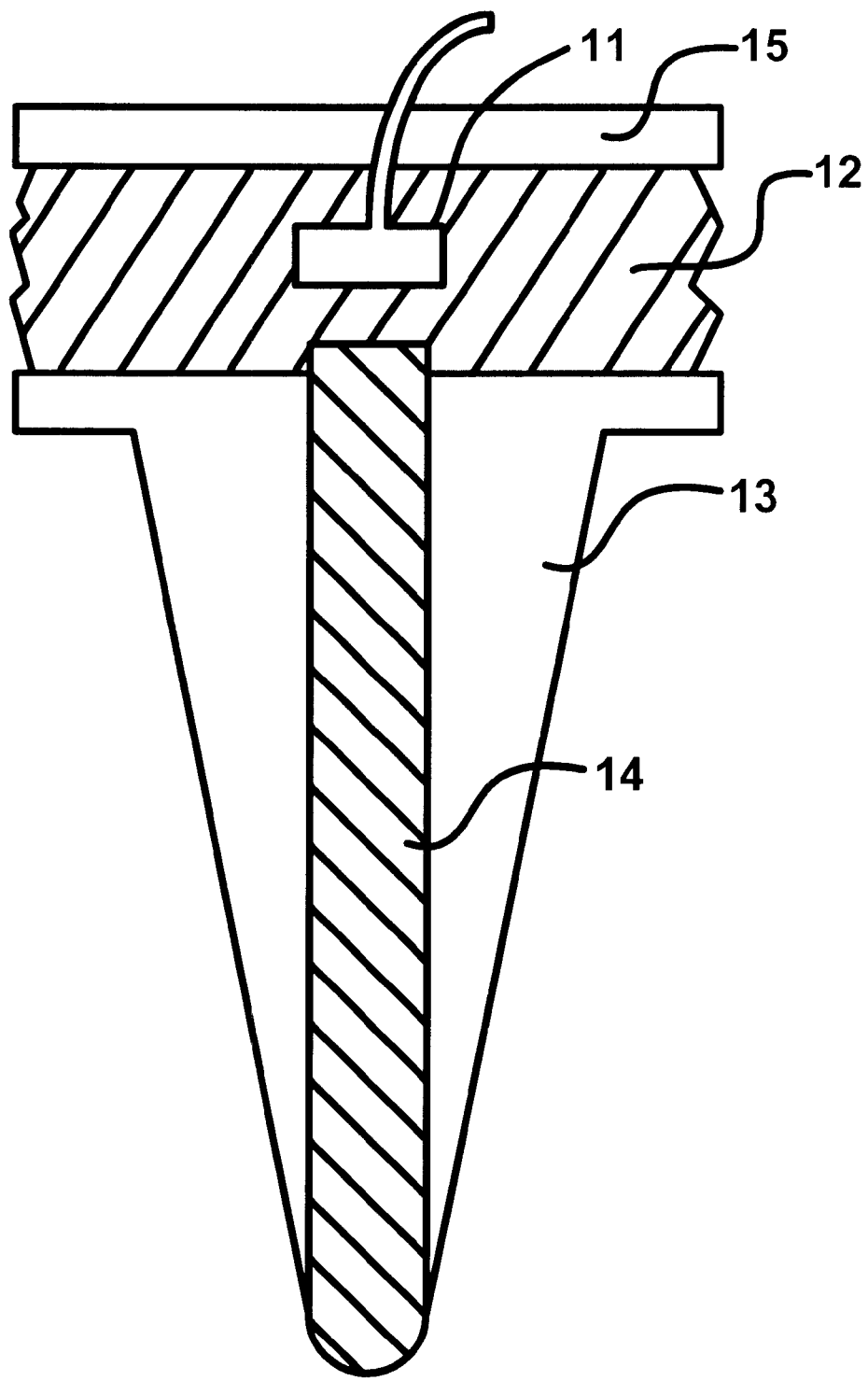
FIG. 1 is a cross-sectional view of an individual elastomeric bristle according to an embodiment of the present invention.

FIG. 1 is a cross-sectional view of an individual elastomeric bristle according to an embodiment of the present invention. As shown, a soft elastomeric bristle 13 contains a wick 14 of suitable material that extends through a channel in the center of the bristle 13. One end of the wick 14 protrudes from the end of the elastomeric bristle 13 to contact a skin surface. The other end of the wick 14 extends past the elastomeric bristle 13 into a fluid reservoir area 12. The fluid reservoir preferably has a sensor top 15 capping it. In the preferred embodiment, the wick material is polyolefin, but other materials are suitable including polyester or nylon.

The wick 14 may be saturated with an electrically conductive liquid, such as a solution of 0.2 to 1.0 molar sodium chloride, potassium chloride, sodium bicarbonate, or other salt solution. The solution serves to conduct the electrical signal obtained from the skin surface to an electrode 11 in the fluid reservoir area 12. The solution may also serve to moisten the skin surface and reduce the electrical resistance of the skin. The solution may also contain a surfactant to facilitate skin moistening, for example, 5 g/liter of sorbitan laurate.

The fluid reservoir 12 may be composed of a porous material capable of holding sufficient solution for the life of the sensor. Alternatively, the fluid reservoir 12 may be a hollow vessel to contain a volume of electrically conductive solution. The wick 14 conducts the solution to the skin surface as the fluid reservoir 12 is gradually depleted. When the fluid reservoir is fully depleted, it may be refilled by a variety of methods including reverse capillary action.

The rheological characteristics of the electrically conductive liquid may be manipulated by selecting specified components to form the electrically conductive liquid's composition. Particular materials may be mixed to create a solution of electrically conductive liquid with a specific viscosity. Additionally, various wick materials may exhibit different capillarity. In constructing the present invention, the composition of the electrically conductive liquid and the wick material may be predetermined for optimum control of the flow rate of the electrically conductive liquid through the wick 14. Flow control preferably determines the amount of skin surface wetting. Optimization of the rate of capillary action and viscosity may be performed to compensate for common chemical products applied to the hair and scalp, such as tonics, dyes, sprays and gels, which may react with the components of the sensor.

Alternatively, the fluid reservoir 12 may also be a volume of porous material loaded with a solution that is in fluidic contact with the wick 14. The material may be of such suitable material as cellulose or nylon.

At the bottom of the fluid reservoir 12, or at the junction of the wick 24 and porous reservoir material, an electrode 11 may be placed to detect the electrical potential conducted through the wick 14. The electrode 11 may be connected to instrumentation capable of amplifying and processing the electrical signal. The electrode 11 may be composed of any electrically conductive material, such as a combination of Ag and AgCl.

Figure 2A:
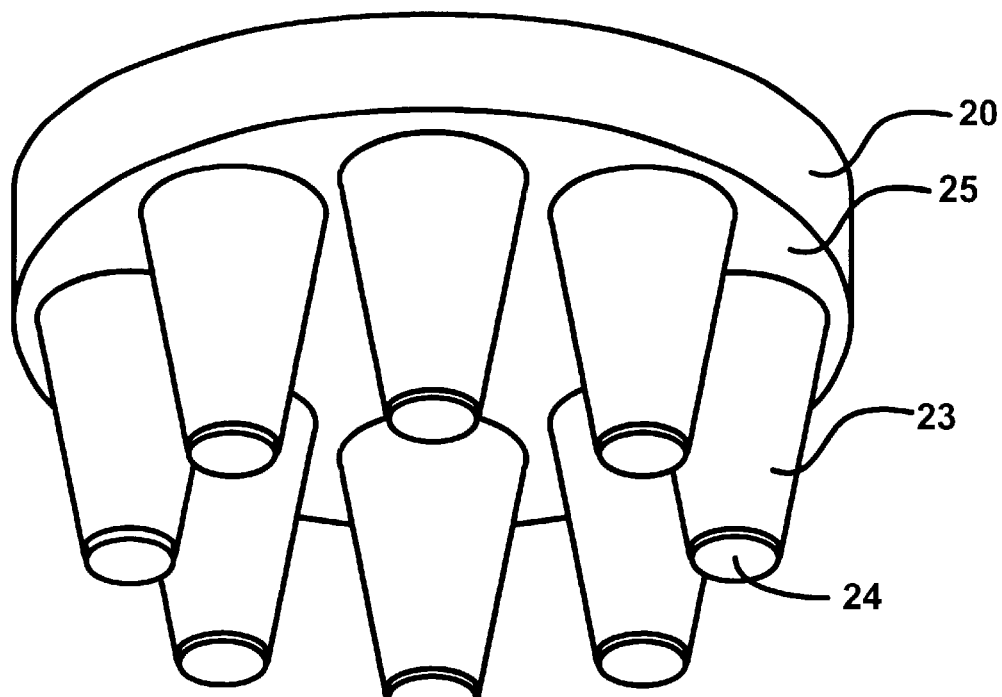
FIGS. 2A and 2B are exterior and interior views, respectively, of a surface comprising a plurality of elastomeric bristles with wicks in accordance with an embodiment of the present invention.
Figure 2B:
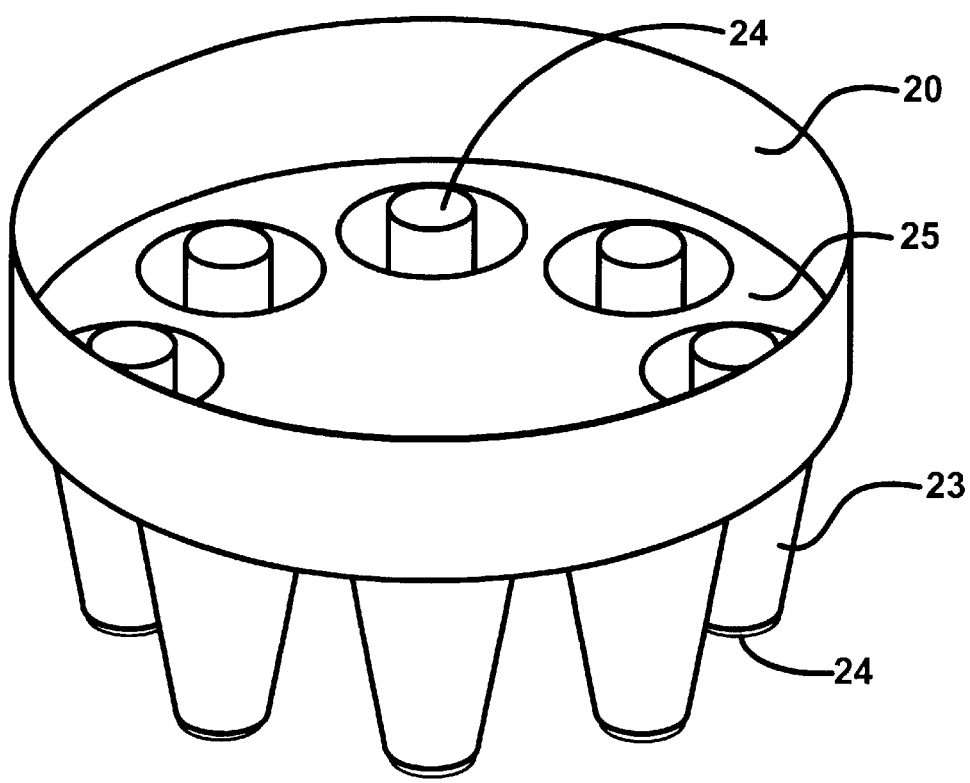

FIGS. 2A and 2B are exterior and interior views, respectively, of a surface comprising a plurality of elastomeric bristles with wicks in accordance with an embodiment of the present invention. As illustrated, a plurality of elastomeric bristles 23 may be physically linked to form a comb 25. The comb 25 is preferably made of a stiff but flexible material such as molded silicon rubber. Each of the elastomeric bristles 23 contains a wick 24 at its core. Each wick 24 may be coupled to a fluid reservoir 12 bound by an outer wall 20. The electrical signals obtained from the elastomeric bristles 23 may be summed in the fluid reservoir 12.

Experimentation has determined that it is not required that every elastomeric bristle 23 on the comb 25 be electrically conductive. In order to achieve a good measurement of biopotential and provide a sensor that is comfortable and securely applied to a skin surface, yet reduce complexity of the device and cost of manufacturing, the comb 25 may be formed with several of the elastomeric bristles 23 as "dummy" bristles that do not provide any electrical conductivity.

Figure 3:
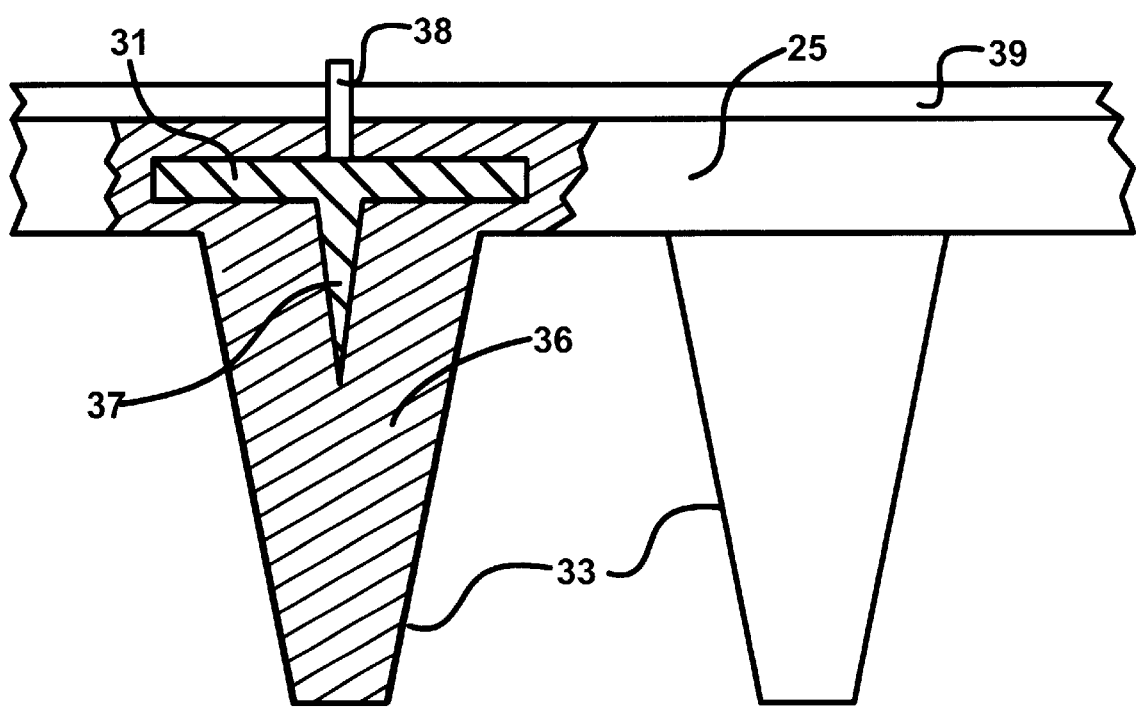
FIG. 3 is a cross-sectional view of an individual elastomeric bristle according to an embodiment of the present invention.

FIGS. 3 is a cross-sectional view of an individual elastomeric bristle according to an embodiment of the present invention. Electrode 31 may be formed such that a large surface area is exposed to the fluid reservoir in order to conduct a strong electrical signal from the bristle 33. The surface area may take the form of a disk. As illustrated, the electrode structure may have conductive spikes 37 positioned to align coaxially with each of the elastomeric bristles 33. One skilled in the art will recognize that many different shapes, for example, a cylinder may be used for the conductive spikes 37. The electrode 37 may provide for a connector 38 to protrude from one side of the disk-shaped electrode 37 and extend externally from the sensor top 39 in order to facilitate connection with external circuitry and a sensor mounting structure.

Alternatively, the material of a porous fluid reservoir may be manufactured in such a way as to have the requisite electrical conductivity as a separate electrode. Preferably, the porous fluid reservoir material may be coated with a combination of Ag and AgCl particles. An electrical connection may then be made between the reservoir material and the measuring instrumentation.

Preferably, the elastomeric bristles 33 are of such a stiffness, or durometer, as to provide for isolation of the sensor from mechanical shock. The end of the elastomeric bristles 33 in contact with a skin surface may remain stationary as the body of the sensor, and the device to which it is coupled, have a certain degree of freedom of movement.

Each elastomeric bristle 33 contains a core 36 of conductive hydrogel that extends through the center of the bristle. One end of the hydrogel core protrudes from the end of the elastomeric bristle 33 to contact the skin surface. The other end of the hydrogel core 36 is in contact with an electrode 37.

The hydrogel material is preferaly formulated to have high electrical conductivity. The hydrogel serves to conduct the electrical signal obtained from the skin surface to the electrode 37. The hydrogel may also serve as a source of moisture to reduce the electrical resistance of the skin surface. The hydrogel may contain a surfactant to facilitate skin moistening.

Figure 4:
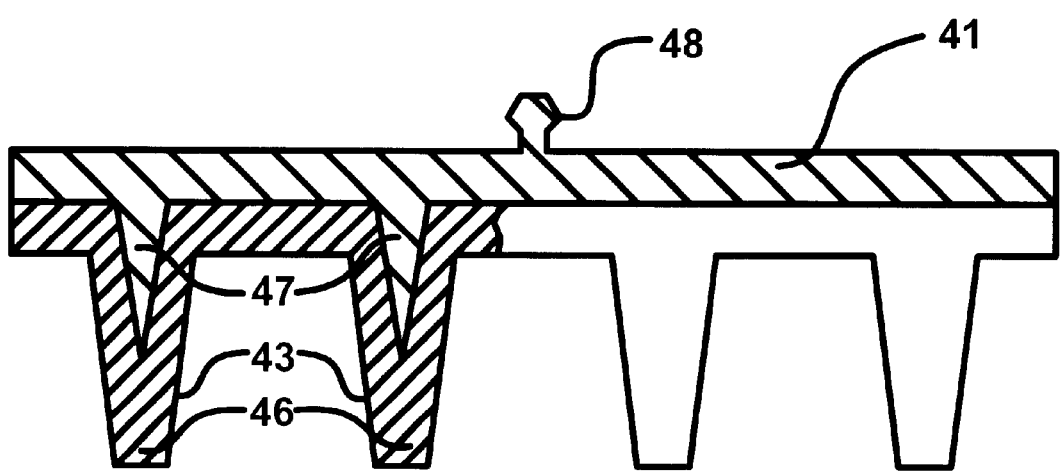
FIG. 4 is a cross-sectional view of elastomeric bristles with an electrode cap according to an embodiment of the present invention.

FIG. 4 is cross-sectional views of elastomeric bristles with an electrode cap according to an embodiment of the present invention. As with the first embodiment, a plurality of elastomeric bristles 43 may be physically linked to form a comb structure. The electrical signals may be obtained from each individual elastomeric bristle 43 and are summed at electrode 41. As shown, the electrode 41 is also the reservoir top.

The electrode 41 may be connected to instrumentation capable of amplifying and processing the electrical signal. The electrode 41 can be composed of any electrically conductive material, for example, a combination of Ag and AgCl.

The electrode 41 may be formed such that a large surface area is exposed to the core 46 of each of the elastomeric bristles 43 in order to conduct a strong electrical signal from the hydrogel. The surface area may take the form of a disk. Additionally, the electrode 41 provides for a connector 48 to protrude from one side of the disk-shaped electrode 41 and extend externally from the sensor in order to facilitate connection with external circuitry and a sensor mounting structure. In a modified electrode structure, conductive spikes 47 may be formed on the face of the disk opposite the connector 48. The conductive spikes 47 may be positioned to align coaxially with each of the elastomeric bristles 43.

Preferably, the elastomeric bristles 43 are of such a stiffness, or durometer, as to provide for isolation of the sensor from mechanical shock. The end of the hydrogel cores 46, in contact with the skin surface, can remain stationary as the body of the sensor, and the device to which it is coupled, have a certain degree of movement.

Figure 5:
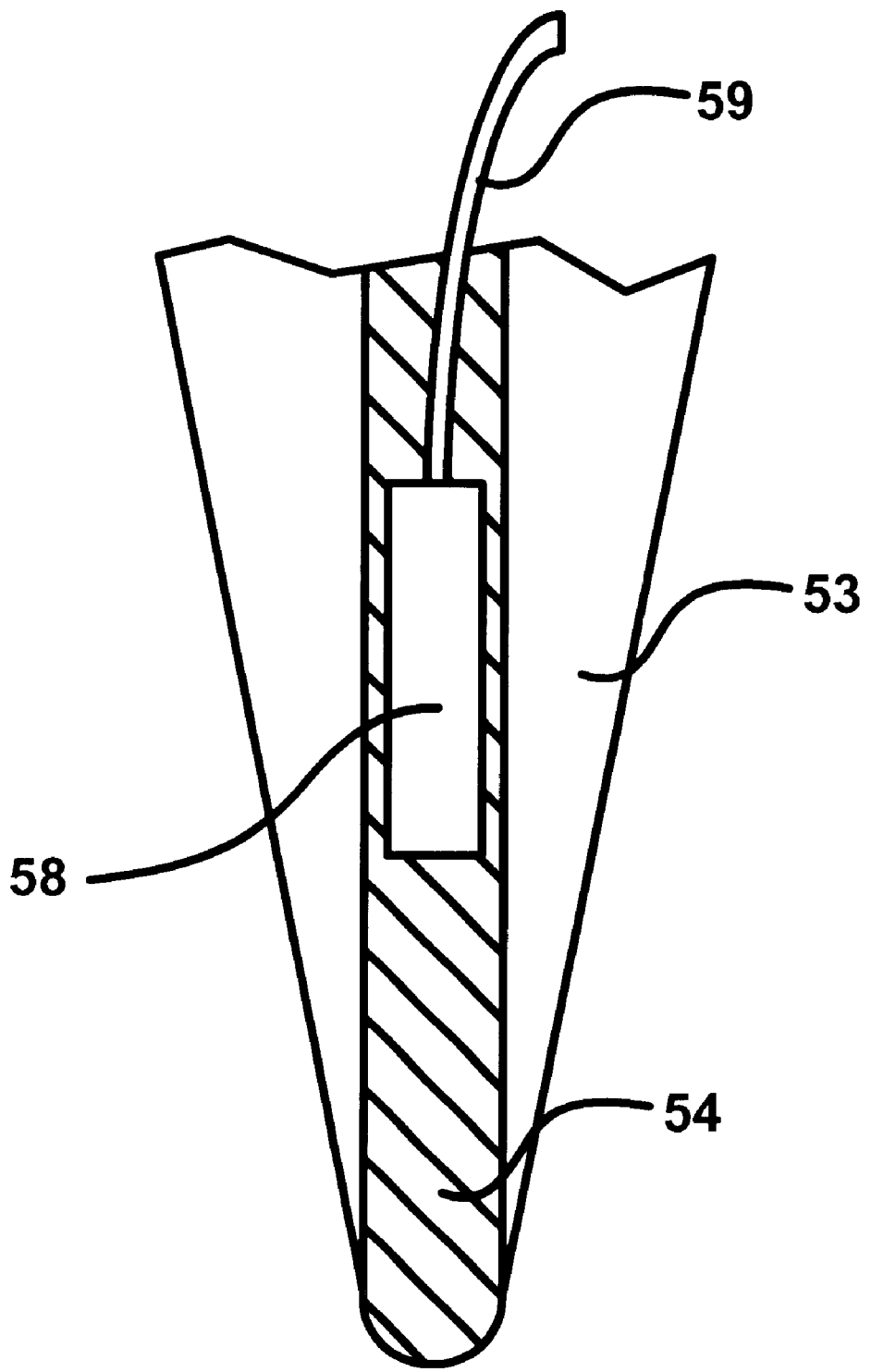
FIG. 5 is a cross-sectional view of an individual elastomeric bristle showing an electrode embedded in the elastomeric bristle according to an embodiment of the present invention.

FIG. 5 is a cross-sectional view of an individual elastomeric bristle 53 showing an electrode 58 embedded in the elastomeric bristle 53 according to an embodiment of the present invention. In this embodiment, the conductive core 54 of the elastomeric bristle 53 may include any conductive material such as a wick or hydrogel. An electrode lead 59 may be used to conduct the signal out of the sensor assembly.

Figure 6:
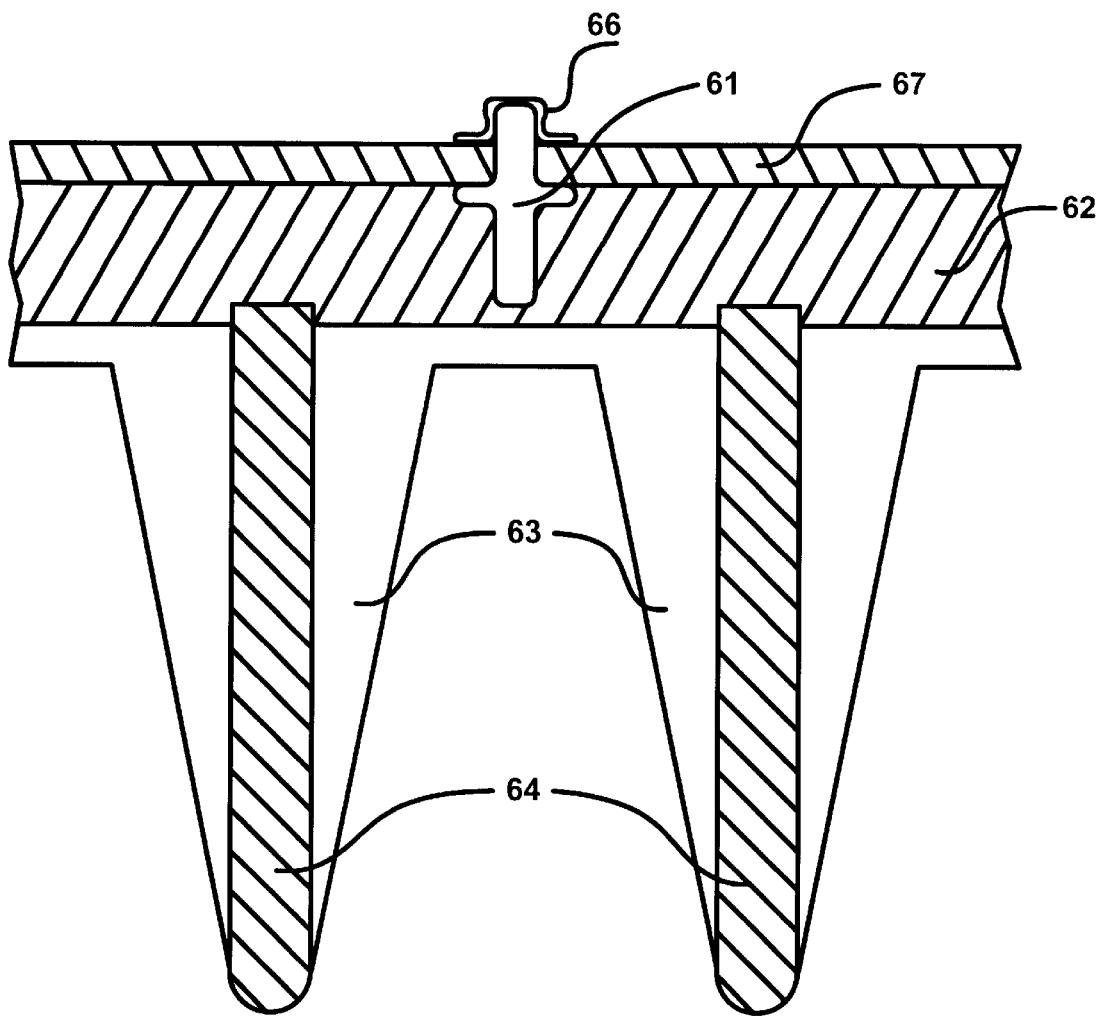
FIG. 6 is a cross-sectional view of an aspect of an embodiment of the present invention showing an electrode and electrode cap fastened to a sensor top.
Figure 7:
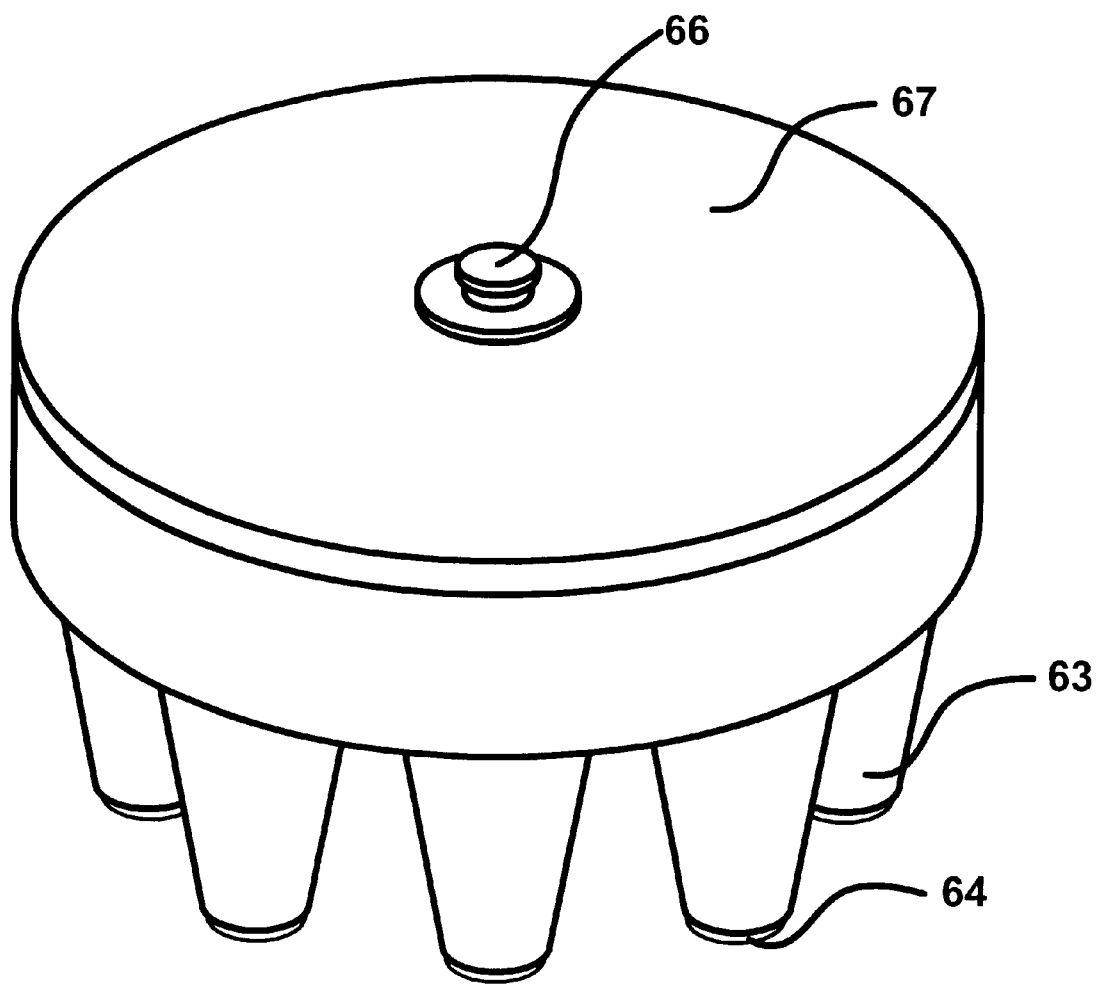
FIG. 7 is an external view of a sensor according to an embodiment of the present invention.

FIG. 6 is a cross-sectional view of an aspect of an embodiment of the present invention showing an electrode 61 and electrode cap 66 fastened to a sensor top 67. In this embodiment, the biopotential signals are conducted up the conductive cores 64 from each of the bristles 63 and are preferably summed in the reservoir 62. FIG. 7 is an external view of a sensor according to the embodiment illustrated in FIG. 6.

For any of the disclosed embodiments of the present invention, the sensor assembly may be disposable like a pen or an ink cartridge for a printer. This allows change over for different users or replacement.

The foregoing descriptions of the preferred embodiments of the present invention have been presented for purposes of illustration and description. They are not intended to be exhaustive or to limit the invention to the precise forms disclosed, and obviously many modifications and variations are possible in light of the above teaching. The illustrated embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A sensor for biopotential measurements comprising:
   a. at least one elastomeric bristle having a base and a tip with a channel running therebetween and a porous wick extending through the channel, said tip adapted to contact a skin surface;
   b. a reservoir formed of a porous material containing an electrically conductive material is formed at the base of said elastomeric bristle and
   c. an electrode for detecting electrical potential wherein said electrode is an electrically conductive coating on said porous material of the reservoir; wherein, said porous wick transports the electrically conductive material from said reservoir to said elastomeric bristle tip in order to conduct an electrical signal obtained from the skin surface, moisten the skin surface, and reduce the electrical resistance of the skin surface.

2. A sensor for biopotential measurements according to claim 1 wherein said electrically conductive coating is a composition comprising Ag and AgCl.

3. A sensor for biopotential measurements comprising:
   a. at least one elastomeric bristle having a base and a tip with a channel running therebetween and a porous wick extending through the channel, said tip adapted to contact a skin surface;
   b. a reservoir containing an electrically conductive material is formed at the base of said elastomeric bristle; and
   c. an electrode for detecting electrical potential placed at the junction of the porous wick and the reservoir;
      wherein, said porous wick transports the electrically conductive material from said reservoir to said elastomeric bristle tip in order to conduct an electrical signal obtained from the skin surface, moisten the skin surface, and reduce the electrical resistance of the skin surface.

4. A sensor for biopotential measurements comprising:
   a. at least one elastomeric bristle having a base and a tip with a channel running therebetween and a porous wick extending through the channel, said tip adapted to contact a skin surface;
   b. a reservoir containing an electrically conductive material is formed at the base of said elastomeric bristle; and
   c. an electrode for detecting electrical potential placed inside the elastomeric bristle channel;
      wherein, said porous wick transports the electrically conductive material from said reservoir to said elastomeric bristle tip in order to conduct an electrical signal obtained from the skin surface, moisten the skin surface, and reduce the electrical resistance of the skin surface.

5. A sensor for biopotential measurements comprising:
   a. at least one elastomeric bristle having a base and a tip with a channel running therebetween and a porous wick extending through the channel, said tip adapted to contact a skin surface;
   b. a reservoir containing an electrically conductive material is formed at the base of said elastomeric bristle; and
   c. an electrode for detecting electrical potential placed in electrical engagement with the reservoir;
      wherein, said porous wick transports the electrically conductive material from said reservoir to said elastomeric bristle tip in order to conduct an electrical signal obtained from the skin surface, moisten the skin surface, and reduce the electrical resistance of the skin surface;
      and further wherein
   d. a plurality of elastomeric bristles are arranged about a surface and internally coupled to said reservoir; and
   e. the biopotential signals obtained from each of said plurality of the bristles are summed in said reservoir.

6. A sensor for biopotential measurements according to claim 5 wherein at least three elastomeric bristles are arranged about said surface.

7. A sensor for biopotential measurements comprising:
   a. a plurality of physically linked elastomeric bristles; and
   b. an electrode for detecting electrical potential placed in electrical engagement with the bristles;
      wherein said plurality of elastomeric bristles comprise at least two different kinds of bristles.

8. A sensor for biopotential measurements according to claim 7 wherein a first kind of elastomeric bristle comprises a base and a tip with a channel running therebetween, said tip adapted to contact a skin surface; and a second kind of elastomeric bristle which is non-conducting.

9. A sensor for biopotential measurements according to claim 8 further comprising:
   a. a porous wick, the porous wick extending through the channel of said first kind of elastomeric bristles; and
   b. a reservoir containing an electrically conductive liquid formed at the base of said elastomeric bristle;
      wherein, said porous wick transports the electrically conductive liquid from said reservoir to said elastomeric bristle tip in order to: conduct an electrical signal obtained from the skin surface, moisten the skin surface, and reduce the electrical resistance of the skin surface.

10. A sensor for biopotential measurements according to claim 8 wherein the channel of said first kind of elastomeric bristles is filled with a hydrogel material having a high electrical conductivity.

11. A sensor for biopotential measurements according to claim 10 wherein said hydrogel material further contains a surfactant.

12. A sensor for biopotential measurements according to claim 8 wherein said electrode is formed at the base of said plurality of elastomeric bristles.

13. A sensor for biopotential measurements according to claim 12 wherein said electrode is made of a composition comprising Ag and AgCl.

14. A sensor for biopotential measurements according to claim 12 wherein said electrode comprises conductive spikes.

15. A sensor for biopotential measurements according to claim 12 wherein said electrode comprises a conductive disk.

16. A sensor for biopotential measurements comprising:
   a. a plurality of physically linked and electrically isolated elastomeric bristles, each having a base and a tip with a channel running therebetween, said tip adapted to contact a skin surface; and
   b. an electrode for detecting electrical potential placed in electrical engagement with the bristles;
      wherein, said channel is filled with a hydrogel material with is formulated to have high electrical conductivity in order to conduct an electrical signal obtained from the skin surface, moisten the skin surface, and reduce the electrical resistance of the skin surface.

17. A sensor for biopotential measurements according to claim 16 wherein said electrode forms a cap at the base of the elastomeric bristles.

18. A sensor for biopotential measurements according to claim 17 wherein said electrode comprises conductive spikes and an electrical connector.

19. A sensor for biopotential measurements according to claim 17 wherein said electrode comprises a conductive disk and an electrical connector.

20. A sensor for biopotential measurements according to claim 16 wherein at least three physically linked and electrically isolated elastomeric bristles are arranged about a surface.

21. A sensor for biopotential measurements according to claim 16 wherein said electrode is made of a composition comprising Ag and AgCl.

* * * * *